United States Patent [19]

Weitz et al.

[11] 4,287,356
[45] Sep. 1, 1981

[54] PREPARATION OF VINYLGLYCOL ESTERS

[75] Inventors: Hans-Martin Weitz, Bad Durkheim; Rolf Fischer, Heidelberg, both of Fed. Rep. of Germany

[73] Assignee: BASF Aktiengesellschaft, Fed. Rep. of Germany

[21] Appl. No.: 97,813

[22] Filed: Nov. 27, 1979

[30] Foreign Application Priority Data

Dec. 15, 1978 [DE] Fed. Rep. of Germany ....... 2854154

[51] Int. Cl.³ ............................................. C07C 67/05
[52] U.S. Cl. ................................................... 560/244
[58] Field of Search ........................................ 560/244

[56] References Cited

U.S. PATENT DOCUMENTS

| 3,671,577 | 6/1972 | Ono | 560/244 |
| 3,755,423 | 8/1973 | Onoda | 560/244 |

FOREIGN PATENT DOCUMENTS

| 2454768 | 5/1976 | Fed. Rep. of Germany . | |
| 1138366 | 1/1969 | United Kingdom | 560/244 |
| 1277837 | 6/1972 | United Kingdom | 560/244 |
| 1487274 | 9/1977 | United Kingdom . | |
| 1494430 | 12/1977 | United Kingdom . | |

OTHER PUBLICATIONS

Kulifay, J. Am. Chem. Soc., 83, pp. 4916–4919 (1961).
"Pure and Applied Chemistry", 43, p. 543 (1975).

Primary Examiner—Natalie Trousof
Assistant Examiner—Michael Shippen
Attorney, Agent, or Firm—Keil & Witherspoon

[57] ABSTRACT

Vinylglycol esters are prepared by reacting butadiene with oxygen and a carboxylic acid in the gas phase or liquid phase over a supported catalyst which contains from 0.1 to 20 percent by weight of palladium and from 2.5 to 7 percent by weight of cobalt.

2 Claims, No Drawings

PREPARATION OF VINYLGLYCOL ESTERS

The present invention relates to a process for the preparation of vinylglycol diesters and monoesters by reacting butadiene with oxygen and a carboxylic acid in the presence of a catalyst containing palladium and cobalt.

It is known that butadiene, oxygen and carboxylic acids may be reacted in the presence of a palladium-containing supported catalyst to give a mixture of isomeric butenediol diesters. These conventional processes give reaction products in which the cis- and trans-but-2-ene-1,4-diol diesters which are important for the preparation of butanediol and tetrahydrofuran greatly predominate, whilst only minor amounts of but-1-ene-3,4-diol diesters (vinylglycol diesters) are formed. For example, the butenediol ester mixtures obtained by the process described in German Published Application DAS No. 2,217,452, using catalysts which in addition to palladium contain antimony, tellurium or bismuth, or the butenediol ester mixtures obtained in accordance with German Laid-Open Application DOS No. 2,417,658, using catalysts containing palladium and tellurium, contain only minor amounts of vinylglycol diacetate.

The vinylglycol acetates, which are sought-after intermediates, may be prepared by isomerizing cis- and trans-but-2-ene-1,4-diol diacetates in the presence of catalysts containing copper or copper compounds (German Laid-Open Application DOS No. 2,406,058) or containing palladium or platinum compounds (German Laid-Open Application DOS No. 2,454,768). The but-2-ene-1,4-diol acetates required for this purpose may be obtained either starting from acetylene (via but-2-yne-1,4-diol and but-2-ene-1,4-diol) or starting from butadiene.

We have found that vinylglycol esters may be prepared by reacting butadiene with oxygen and a carboxylic acid in the gas phase or liquid phase over a palladium-containing supported catalyst, if the catalyst used contains from 0.1 to 20 percent by weight of palladium and from 2.5 to 7 percent by weight of cobalt.

For the preparation of vinylglycol diacetate and the corresponding monoacetates, the reaction can be represented by the following equation, where $-OAc = -O-CO-CH_3$.

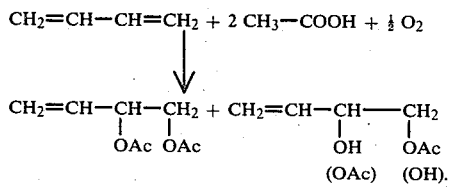

Using the process according to the invention, butadiene is reacted with oxygen and a carboxylic acid to give, with high selectivity, a mixture of but-1-ene-3,4-diol diesters and monoesters (ie. vinylglycol diesters and monoesters). This result is surprising, since preferential formation of the but-2-ene-1,4-diol diesters would have been expected. Further, it is advantageous that vinylglycol diacetates and vinylglycol monoacetates may be obtained in a single reaction step from butadiene, so that isomerization of the but-2-ene-1,4-diol diacetates to the but-1-ene-3,4-diol diacetates is unnecessary, and that the but-2-ene-1,4-diol diacetates, formed to a minor degree, can readily be removed by distillation.

According to the novel process, the reaction is carried out with butadiene or with a hydrocarbon mixture which in addition to butadiene may contain monoolefins and paraffinic hydrocarbons. Instead of pure oxygen, an oxygen-containing inert gas may be used. Examples of carboxylic acids employed are fatty acids, especially formic acid, acetic acid and propionic acid, amongst which acetic acid is particularly preferred, for economic reasons.

The reaction temperature is usually from 50° to 180° C. If the reaction is carried out in the gas phase, it is preferably from 120° to 150° C., whilst if the reaction is carried out in the liquid phase it is, for example, from 70° to 110° C. The reaction pressure is determined by the procedure used and may be from atmospheric pressure to, for example, 100 bar.

The supported catalysts may be prepared, for example, by the method conventionally used for supported palladium catalysts. For example, the carrier is dispersed in a solution which contains a palladium compound and a cobalt compound, the solvent is evaporated and the residue is reduced in a stream of gas comprising, for example, hydrogen or nitrogen laden with a reducing compound, eg. hydrazine, methanol or formaldehyde. The dried catalyst can also be reduced with a liquid reducing agent.

An alternative method of preparation of the catalyst is to treat a mixture of the carrier and the solution with a precipitant, for example an alkaline precipitant, and to isolate and reduce the precipitate.

A very useful method for the preparation of the catalyst is to precipitate the metal directly from an aqueous salt solution by means of a reducing agent, eg. formaldehyde, hydrazine and the like, at a suitable pH (cf., for example, J.Amer. Chem. Soc. 83 (1961), 4,916). Advantageously, the crude catalyst thus obtained is additionally heated to an elevated temperature in a reducing gas stream.

The palladium and the cobalt may be deposited on the carrier either simultaneously or in optional sequence. In some cases, the carrier may be added in the form of a soluble compound and be coprecipitated with the active metal. The reducing process used may be any by means of which palladium and cobalt can be converted to the metallic state.

Examples of suitable carriers are active charcoal, bauxite, pumice, silica gel, kieselguhr and other forms of silica, magnesia, clay and alumina. The functional performance of the carrier may sometimes be improved by a conventional pretreatment, for example with an acid. Active charcoal has proved to be a particularly preferred carrier.

In preparing the catalyst, the nature of the palladium compound is immaterial. For example, a halogen-containing palladium compound, eg. palladium chloride, a salt of an organic acid, eg. palladium acetate, a nitrate, an oxide or the like may be used. However, other palladium compounds, especially complex compounds, are also suitable starting materials. The cobalt can, likewise, be introduced in the form of virtually any compound into the catalyst to be prepared. In general, soluble compounds are employed, for convenience.

To prepare particularly active catalysts, it has proved advantageous to heat the catalyst at 400°–900° C. for from 15 minutes to 4 hours. Since the heating ultimately results in a certain stabilization of the catalytically active state, once the latter has been attained, it is in general not necessary to adhere to a particular maximum period of heating. If the carrier or the metals tend to oxidize under the heating conditions, heating is advantageously carried out in the presence of a reducing atmosphere, for example in pure hydrogen. The success achieved by the heat treatment can in each case be assessed either by determining the catalytic activity or by determining the X-ray structure.

The reaction to be catalyzed may be carried out batchwise or continuously, by any conventional method, for example using a fixed bed, fluidized bed or threephase fluidized bed, depending to some extent on the particular state of aggregation of the reaction mixture.

If the activity of the catalyst diminishes after a certain period of operation, it can in many cases be restored by suitable methods, for example, a deposit of polymeric compounds on the catalyst can be removed by means of suitable solvents or by careful treatment with an oxygen-containing gas. If the activity of the catalyst has been reduced by oxidation processes, regeneration can often be achieved by treatment with a reducing compound, eg. hydrazine, formaldehyde, hydrogen, carbon monoxide, methanol (vapor) and the like.

The vinylglycol diacetates and vinylglycol monoacetates obtainable by the process of the invention are valuable intermediates, for example for the preparation of 4-acetoxy-2-methyl-crotonaldehyde which is used as a $C_5$ unit in the synthesis of vitamin A acetate (Pure and Applied Chemistry, 43 (1975), 543).

In the Examples which follow, parts are by weight.

EXAMPLE 1

(a) Preparation of the catalyst 13.75 parts of $CoBr_2.6H_2O$ are dissolved in 100 parts of water and the solution is added, at room temperature, to a solution of 4.17 parts of $PdCl_2$ in 200 parts by volume of 6N hydrochloric acid. The mixed salt solution is then added at room temperature to 50 parts of active charcoal (0.3–0.5 mm, 35–50 mesh), which has been pretreated by mixing, at room temperature, with 160 parts by volume of 15 percent strength nitric acid, heating to 70° C., stirring for 5 hours at this temperture, cooling, collecting on a glass suction filter, washing with water until the pH is 7–8, and drying for 20 hours in an oven under reduced pressure. The mixture of the salt solution and the active charcoal is evaporated to dryness at 85° C. on a rotary evaporator, under reduced pressure from a waterpump.

The catalyst is then dried for 2 hours at 150° C. in an oven under reduced pressure, followed by 2 hours at 150° C. under a stream of nitrogen. It is then activated by heating for 6 hours at 200° C., followed by 6 hours at 400° C., in nitrogen saturated with methanol at room temperature, and thereafter for 0.5 hour in hydrogen at 800° C. The catalyst is then cooled to room temperature under a stream of nitrogen, after which it is stored under argon in a bottle which can be sealed efficiently. According to analysis to determine the metals, the catalyst contains 5.88% of palladium and 5.14% of cobalt.

(b) Preparation of vinylglycol acetates 15 parts of the catalyst prepared as described in paragraph (a) are suspended in 600 parts of glacial acetic acid and the suspension is introduced into a three-necked flask equipped with a gassing stirrer, internal thermometer, reflux condenser, gas inlet tube and dropping funnel. It is then heated, under a stream of nitrogen, to 95° C. on an oil bath. At this temperature, 3,000 parts by volume of butadiene per hour and 3,000 parts by volume of oxygen per hour are introduced simultaneously, for 4 hours, through the gas inlet tube. After completion of addition of the starting materials, stirring is continued for 15 minutes whilst passing nitrogen through the flask, the reaction mixture is then allowed to cool to room temperature, and the catalyst is filtered off on a glass suction filter. This gives 547 parts of a reaction product which, according to analysis by gas chromatography, contains 1.89 parts of but-1-ene-3,4-diol diacetate and 8.85 parts of but-1-ene-3,4-dio monoacetates (91.9% of but-1-ene-3,4-diol compounds based on all acetate compounds formed). Of the 29 parts of butadiene employed, 5.93 parts (20.4%) are converted. The yield of butene-3,4- and 1,4-diol diacetates and monoacetates is 78.4% based on butadiene converted.

COMPARATIVE EXAMPLES 2a AND 2b

Two catalysts, respectively containing 4.02% of palladium and 2.2% of cobalt, and 4.78% of palladium and 7.42% of cobalt, on active charcoal, are prepared by the method of Example 1 (a), the amounts of $CoBr_2.6H_2O$ and $PdCl_2$ being varied. The results achieved by acetoxylating butadiene in the presence of these catalysts under the conditions of Example 1 (b) are shown in the Table.

EXAMPLES 3 TO 5

Catalysts containing 5–5.6% of palladium and 3.6–5.6% of cobalt on active charcoal as the carrier are prepared by the method of Example 1 (a), the amounts of $CoBr_2.6H_2$ and $PdCl_2$ being varied. The experimental results achieved by acetoxylating butadiene in the presence of these catalysts under the conditions of Example 1 (b) are shown in the Table.

TABLE

Acetoxylation of butadiene in the presence of Pd/Co catalysts

| Example | Catalyst % Pd | % Co | 3,4-BEDA [parts] | 3,4-BEMA [parts] | cis-1,4-BEDA [parts] | trans-1,4-BEDA [parts] | Proportion of 3,4- isomers [mole %] | Butadiene Conversion employed [parts] | [%] | Yield [%] |
|---|---|---|---|---|---|---|---|---|---|---|
| 2 a | 4.02 | 2.2 | 2.04 | 0.41 | 1.93 | 8.98 | 19 | 30 | 42.3 | 33 |
| 2 b | 4.78 | 7.42 | 3.69 | 0.84 | 3.47 | 19.4 | 17 | 30 | 57.7 | 50 |
| 3 | 5.06 | 3.56 | 1.72 | 5.83 | 0.24 | 1.41 | 85 | 29 | 18.9 | 64 |
| 4 | 4.98 | 5.48 | 2.25 | 5.26 | 0.33 | 1.69 | 82 | 28 | 16.8 | 75 |
| 5 | 3.19 | 5.61 | 2.05 | 10.17 | 0.21 | 1.24 | 91 | 27 | 20.7 | 95 |

3,4-BEDA = but-1-ene-3,4-diol diacetate
3,4-BEMA = but-1-ene-3,4-diol monoacetate
cis-1,4-BEDA = cis-but-2-ene-1,4-diol diacetate
trans-1,4-BEDA = trans-but-2-ene-1,4-diol diacetate

We claim:

1. A process for the preparation of vinylglycol esters by reacting butadiene with oxygen and a carboxylic acid selected from the group consisting of formic acid, acetic acid and propionic acid in the liquid phase over a palladium-containing supported catalyst, wherein the catalyst used contains from 0.1 to 20 percent by weight of palladium and from 2.5 to 7 percent by weight of cobalt and has been heated at 400°–900° C. for from 15 minutes to 4 hours.

2. The process of claim 1, wherein the catalyst used contains from 1 to 6 percent by weight of palladium and from 3.5 to 6 percent by weight of cobalt.

* * * * *